(12) United States Patent
Han

(10) Patent No.: US 6,961,436 B1
(45) Date of Patent: Nov. 1, 2005

(54) NOISE-PROTECTING ARRANGEMENT FOR EAR PROTECTOR

(76) Inventor: David Han, 2F, No.32, Lane 295, Sec. 1, Tun Hua S. Rd., Taipei (TW)

( * ) Notice: Subject to any disclaimer, the term of this patent is extended or adjusted under 35 U.S.C. 154(b) by 6 days.

(21) Appl. No.: 10/815,841

(22) Filed: Apr. 2, 2004

(51) Int. Cl.⁷ .................... H03G 3/00; A61F 11/06; H04R 1/10
(52) U.S. Cl. .................. 381/104; 381/72; 381/74; 381/107
(58) Field of Search ................ 381/104, 107, 381/74, 72

(56) References Cited

U.S. PATENT DOCUMENTS

| 4,536,888 A | * | 8/1985 | Wilson | 379/395 |
| 4,918,745 A | * | 4/1990 | Hutchison | 455/41.2 |
| 2005/0094824 A1 | * | 5/2005 | Chuang | 381/72 |

* cited by examiner

*Primary Examiner*—Sinh Tran
*Assistant Examiner*—Devona E Faulk
(74) *Attorney, Agent, or Firm*—Troxell Law Office, PLLC

(57) ABSTRACT

A noise-protecting arrangement for ear protector includes an audio-frequency receiving unit, a first audio-frequency amplifying unit, a volume control amplifying unit, a current amplifying unit, a gain control signal unit, an impedance matching unit, a gain control unit, a gain adjusting unit, a volume regulating unit, a second audio-frequency amplifying unit, and an audio-frequency output unit. The noise-protecting arrangement automatically attenuates a noise that enters into the ear protector and is higher than a predetermined dB level, and thereby protects a user's eardrum. The ear protector with this noise-protecting arrangement is suitable for use in environments in which various machine tools, such as drills, millers, lathes and the like are operated, firing training is performed, high-pressure air horn, vehicles, and aircrafts are maintained, or other types of high-frequency noises exist.

3 Claims, 2 Drawing Sheets

NOISE-PROTECTING ARRANGEMENT FOR EAR PROTECTOR

FIELD OF THE INVENTION

The present invention relates to a noise-protecting arrangement for ear protector. The noise-protecting arrangement includes an audio-frequency receiving unit, a first audio-frequency amplifying unit, a volume control amplifying unit, a current amplifying unit, a gain control signal unit, an impedance matching unit, a gain control unit, a gain adjusting unit, a volume regulating unit, a second audio-frequency amplifying unit, and an audio-frequency output unit to automatically attenuate a noise that enters into the ear protector and is higher than a predetermined dB value, and thereby protects a user's eardrum.

BACKGROUND OF THE INVENTION

Currently, there are many differently structured ear protectors available in the market for protecting users' ears against impairment by noises. However, most of these conventional ear protectors are designed only to isolate noises above a predetermined dB level. That is, when a user wearing the ear protectors works in a noisy environment, he or she is completely isolated from any external sound having an audio frequency higher than the predetermined dB level.

SUMMARY OF THE INVENTION

A primary object of the present invention is to provide a noise-protecting arrangement for ear protector that is adapted to automatically attenuate a noise that enters into the ear protector and is higher than a predetermined dB level, instead of completely isolating the audio signal, so that a user wearing the ear protector may still hear all sounds in the environment while being safely protected against impaired eardrums.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
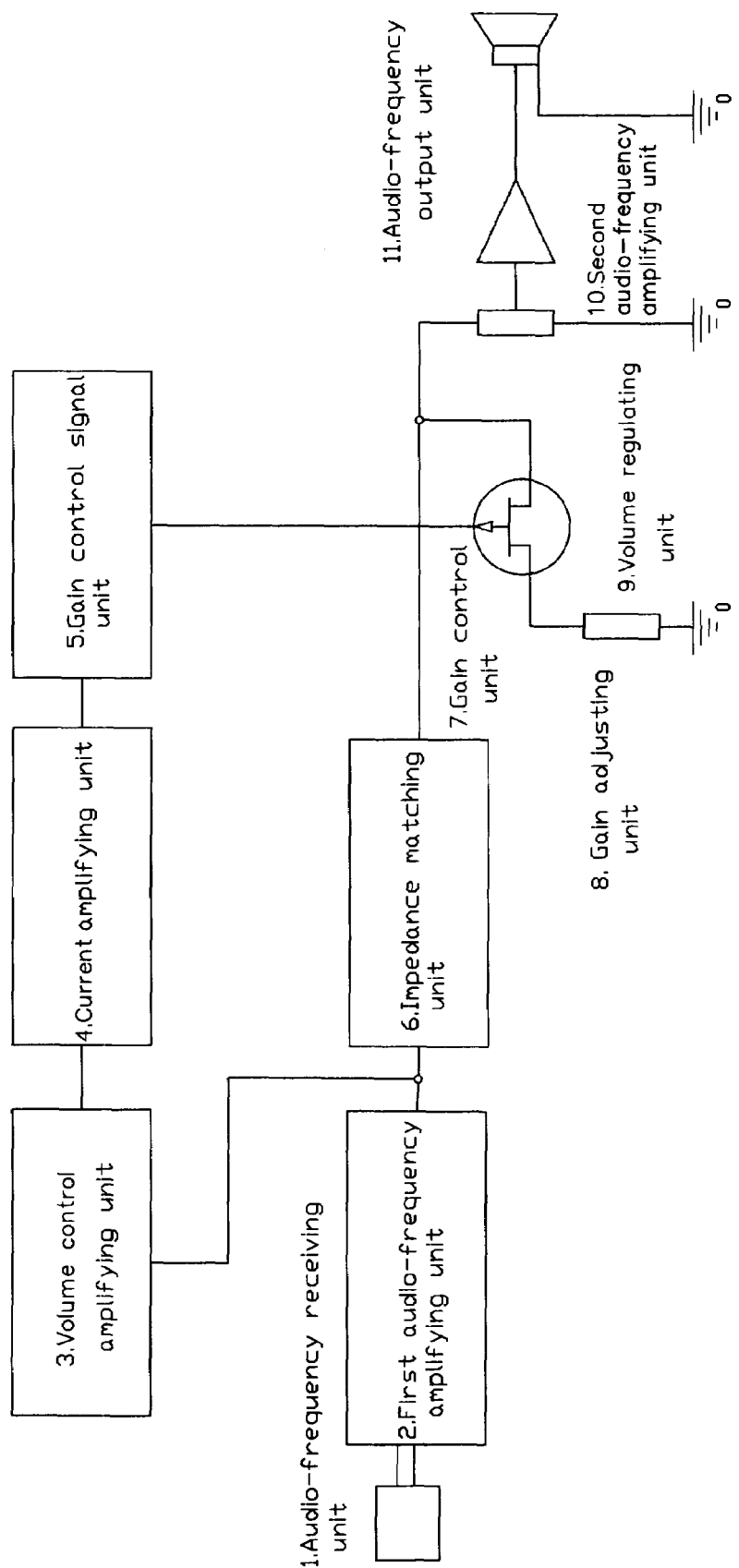
FIG. 1 is a block diagram showing a circuitry for receiving audio signals according to the present invention.
Figure 2:
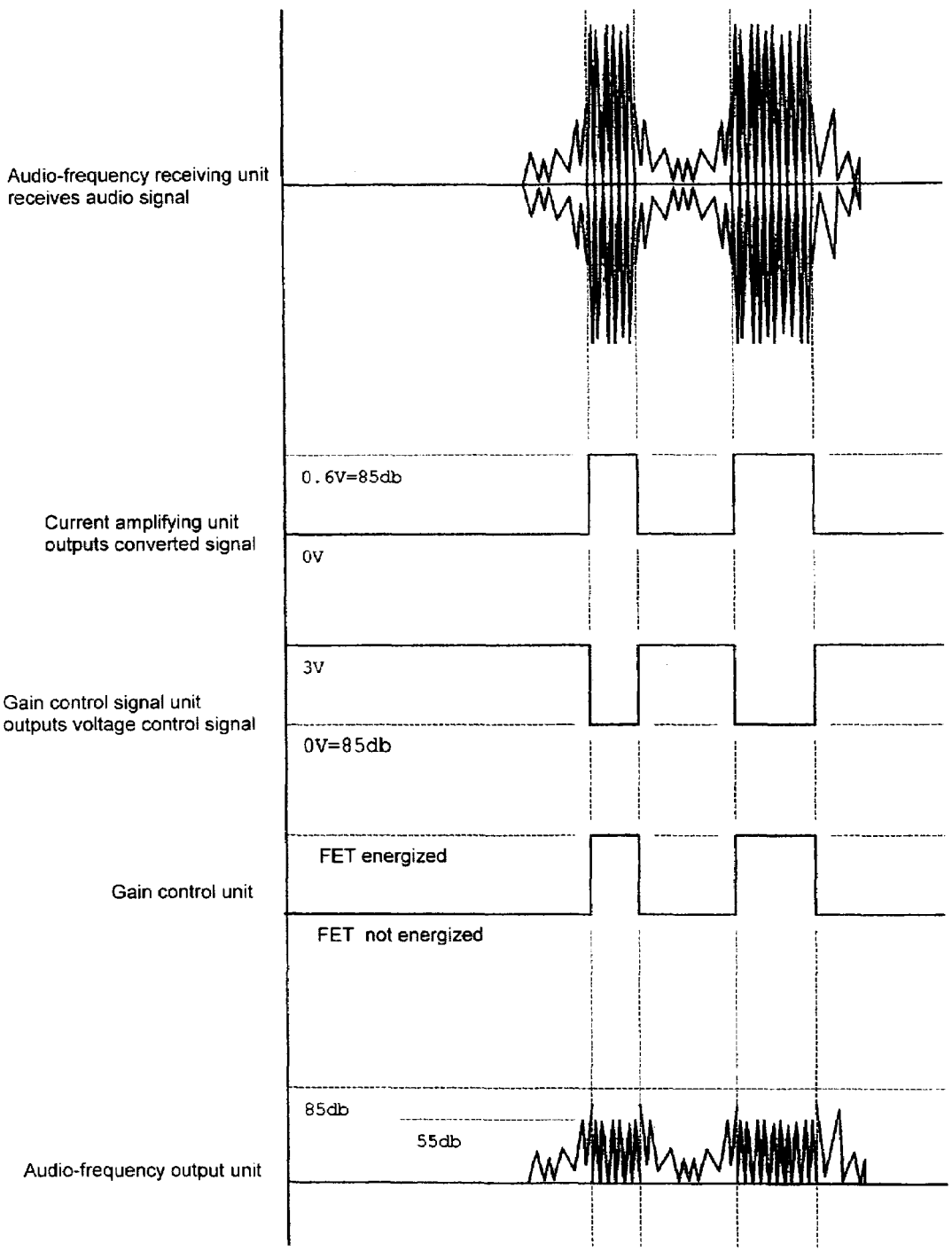
FIG. 2 shows wave shapes generated at different circuit stages of the present invention.

Please refer to FIG. 1 that is a block diagram showing a circuitry for receiving audio signals according to the present invention, and to FIG. 2 that shows wave shapes generated at different circuit stages of the present invention. As shown, the present invention mainly includes an audio-frequency receiving unit 1, a first audio-frequency amplifying unit 2, a volume control amplifying unit 3, a current amplifying unit 4, a gain control signal unit 5, an impedance matching unit 6, a gain control unit 7, a gain adjusting unit 8, a volume regulating unit 9, a second audio-frequency amplifying unit 10, and an audio-frequency output unit 11.

The audio-frequency receiving unit 1 may be, for example, a capacitor microphone for receiving an external audio signal. The external audio signal received by the audio-frequency receiving unit 1 is sent to and amplified by the first audio-frequency amplifying unit 2. The external audio signal amplified by the first audio-frequency amplifying unit 2 is then sent to the volume control unit 3 for amplification again. The audio signal further amplified by the volume control unit 3 is then sent to and processed at the current amplifying unit 4. The audio signal processed at and output from the current amplifying unit 4 is of 85 dB, which is equivalent to an audio signal of 0.6V.

The audio signal of 0.6V so obtained from the current amplifying unit 4 is sent to and received by the gain control signal unit 5, at where the audio signal is processed, converted, and output as a control signal of 0V. When a sound source received by the gain control signal unit 5 is an audio signal less than 85 dB, the converted and output audio signal shall be a control signal of 3V.

The impedance matching unit 6 is adapted to receive an audio signal amplified by the first audio-frequency amplifying unit 2, and the received audio signal is matched and given an impedance to reduce audio signal loss thereof.

The gain control unit 7 is a field effect transistor (EFT). When the audio signal received, processed, converted, and output by the gain control signal unit 5 to the gain control unit 7 is a control signal of 0V, the gain control unit 7 is energized for the audio signal amplified by the impedance matching unit 6 to attenuate at the gain adjusting unit 8 and then pass through the volume regulating unit 9. On the other hand, when the audio signal received, processed, converted, and output by the gain control signal unit 5 to the gain control unit 7 is a control signal of 3V, the gain control unit 7 is not energized and the audio signal amplified by the impedance matching unit 6 is allowed to directly pass through the volume regulating unit 9.

The gain adjusting unit 8 is a fixed resistance for adjusting the value of gain of the audio signal attenuated by the gain adjusting unit 8.

The volume regulating unit 9 is a variable resistance for regulating an intensity of the audio signal passed through the impedance matching unit 6, so as to control high and low of volume of the audio signal being output.

The second audio-frequency amplifying unit 10 is used to amplify the audio signal regulated by the volume regulating unit 9.

The audio-frequency output unit 11 is a loudspeaker. When the audio signal is processed at the second audio-frequency amplifying unit 10, the audio signal initially received by the audio-frequency receiving unit 1 could be heard at the loudspeaker of the audio frequency output unit 11.

With the above arrangements, it is possible to attenuate the volume output of noise to protect a user's eardrum against impairment.

What is claimed is:

1. A noise-protecting arrangement for ear protector, comprising:
    an audio-frequency receiving unit, which is a capacitor microphone for receiving an external audio signal;
    a first audio-frequency amplifying unit for amplifying the audio signal received by said audio-frequency receiving unit;
    a volume control amplifying unit for further amplifying the audio signal having been amplified by said first audio-frequency amplifying unit;
    a current amplifying unit for processing the audio signal received from said volume control amplifying unit, so that the audio signal processed, converted, and output by said current amplifying unit is of 85 dB, which is equivalent to an audio signal of 0.6V;

a gain control signal unit for processing the 0.6V audio signal output from said current amplifying unit, so that the audio signal processed, converted, and output by said gain control signal unit is a control signal of 0V;

an impedance matching unit for matching the audio signal having been amplified by said first audio-frequency amplifying unit, so that said amplified audio signal is given an impedance to reduce loss of the audio signal;

a gain control unit, which is a field effect transistor (FET) and is energized when the audio signal processed, converted, and output by said gain control signal unit to said gain control unit is a control signal of 0V, so that the audio signal amplified by said impedance matching unit is attenuated at a gain adjusting unit and then passes through a volume regulating unit;

a volume regulating unit, which is a variable resistance for regulating an intensity of the audio signal passed through said impedance matching unit and thereby controlling high and low of volume of the audio signal being output;

a second audio-frequency amplifying unit for amplifying the audio signal having been regulated by said volume regulating unit; and an audio-frequency output unit, which is a loudspeaker, at where the audio signal received by said audio-frequency receiving unit and processed by said second audio-frequency amplifying unit may be heard.

2. The noise-protecting arrangement for ear protector as claimed in claim 1, wherein said gain control signal unit is adapted to converts and outputs the audio signal as a control signal of 3V when a sound source received by said gain control signal unit is an audio signal of less than 85 dB.

3. The noise-protecting arrangement for ear protector as claimed in claim 1, wherein said gain control unit is not energized when the audio signal converted and output by said gain control signal unit to said gain control unit is a control signal of 3V, allowing the audio signal amplified by said impedance matching unit to directly pass through said volume regulating unit.

* * * * *